United States Patent [19]
Nordan

[11] Patent Number: 4,917,681
[45] Date of Patent: * Apr. 17, 1990

[54] INTRAOCULAR MULTIFOCAL LENS

[76] Inventor: Lee T. Nordan, 9834 Genesee Ave., Ste. 209, La Jolla, Calif. 92037

[*] Notice: The portion of the term of this patent subsequent to Sep. 6, 2005 has been disclaimed.

[21] Appl. No.: 232,140

[22] Filed: Aug. 15, 1988

Related U.S. Application Data

[63] Continuation of Ser. No. 88,227, Aug. 24, 1987, Pat. No. 4,769,033.

[51] Int. Cl.⁴ .............................................. A61F 2/16
[52] U.S. Cl. ...................................................... 623/6
[58] Field of Search ................ 623/6; 351/161, 160 R

[56] References Cited

U.S. PATENT DOCUMENTS

| | | | |
|---|---|---|---|
| 3,866,249 | 2/1975 | Flom | 623/6 |
| 3,950,082 | 4/1976 | Volk | 351/161 |
| 4,418,991 | 12/1983 | Breger | 351/161 |
| 4,450,593 | 5/1984 | Poler | 623/6 |
| 4,504,982 | 3/1985 | Burk | 623/6 |
| 4,640,595 | 2/1987 | Volk | 351/160 R |
| 4,666,446 | 5/1987 | Koziol | 623/6 |
| 4,769,033 | 9/1988 | Nordan | 623/6 |

OTHER PUBLICATIONS

Norman S. Jaffe et al., "Pseudophakos", published by the C. U. Mosby Company, 1978, Chap. 6, pp. 58, 59 and 60.

"Ocular Surgery News", Jun. 1, 1987, vol. 5, No. 11, pp. 1,14 and 15, Article "No Near Corrections Needed by Almost 50 in Bifocal IOL Series".

"Ocular Surgery News", Jun. 1, 1987, vol. 5, No. 11, pp. 1, 12 and 13, Article Bifocal IOL Implanted in England; U.S. Trial May Begin This Month.

Primary Examiner—Richard J. Apley
Assistant Examiner—James Prizant
Attorney, Agent, or Firm—Henri J. A. Charmasson

[57] ABSTRACT

An intraocular lens, in form of a disk, intended to replace the crystalline lens of a patient's eye, in particular after a cataract extraction, comprises on its distal side an aspherical sector extending approximately from the midline of the disk over one quarter of the surface thereof. The rest of the distal side is spherical. The radius of curvature of the aspherical sector varies monotonously between the value of the radius of the spherical sectors and a lower value. Such a configuration allows light rays impinging on the intraocular lens to be refracted at different angles and provides both near and distance vision. The discontinuity at transition between the aspherical sector and the spherical sector is blocked out by dark or etched plastic to eliminate glare. The proximal side can either be a convex surface, a concave surface or a plane.

6 Claims, 2 Drawing Sheets

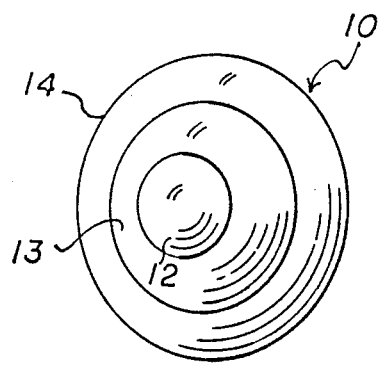
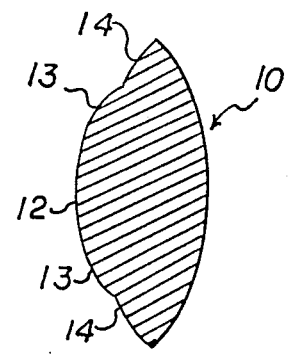
FIG.10  FIG.11
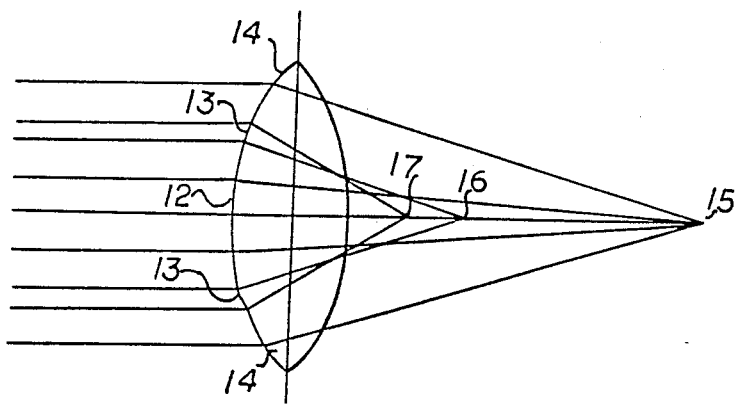
FIG.12

INTRAOCULAR MULTIFOCAL LENS

PRIOR APPLICATION

This application is a continuation application of pending prior application Ser. No. 088,227 filed on Aug. 24, 1987 for a Intraocular Multifocal lens, now U.S. Pat. No. 4,769,033.

FIELD OF THE INVENTION

The invention relates to aphakic lenses and more particularly to aphakic intraocular lenses.

BACKGROUND OF THE INVENTION

Intraocular lenses have been increasingly used in the last decade, in particular in aphakic patients after a cataract operation. Intraocular lenses provide many advantages over both spectacle and contact lenses. They permit a better elimination of perceptual problems and reduce image size disparity. Since the intraocular lens is intended to remain in situ, it eradicates the difficulties in inserting and removing contact lenses encountered by elderly patients. The use of an intraocular lens may also be advantageous for those working in unusual environments and for those whose visual requirements for occupation must be fulfilled. Presently, opthamologists and eye surgeons recommend that intraocular implant lens surgery be performed when the patient is not likely to manage a contact lens.

According to Norman S. Jaffe et al, "Psudophakos", published by The C.V. Mosby Company, 1978, the majority of patients who undergo lens implant surgery in the United States receive implants whose power is estimated from the basic refraction of the eye. Experience has shown however that there are many pitfalls in estimating the basic refraction in this way, in view of the high incidence of residual anisometropia and aniseikonia cases in patients thus corrected. More recently ophthalmologists surgeons have endeavoured to design bifocal intraocular lenses (IOL hereinafter) to focus both the near and far images on the retina. The "Ocular Surgery News", June 1, 1987, Volume 5, Number 11, reports the latest findings concerning bifocal IOL's. These IOL's, however, provide near and distance vision but do not provide a continuum in the dioptric range. To the best of the inventor's knowledge, there is not known any multifocal intraocular lens.

SUMMARY OF THE INVENTION

It is therefore an object of this invention to provide a new multifocal intraocular lens with a full dioptric range.

It is also another object of the present invention to produce an intraocular lens which can be easily and safely implanted in a patient's eye and which can provide optimal post-operative vision.

Another object is to provide an intraocular lens which can be easily manufactured and can be produced at low cost.

Another object of the present invention is also to furnish an intraocular lens which is more particularly designed for the surgical correction of aphakia following extracapsular cataract exraction.

In accordance with the present invention, an intraocular lens has the general shape of a biconvex disk. The proximal side, to be placed against the vitreous humor is substantially spherical, whereas the distal side is composed of three sectors. The upper sector is essentially spherical and extends to the midsection of the disk. The center sector, adjacent the upper sector, extends therefrom to the lower quarter of the disk and is formed of an aspherical sector of decreasing radius of curvature. The lower sector is also essentially spherical. Such a configuration allows light rays impinging on the intraocular lens to be refracted at different angles. The focal plane thus varies continuously between a near focal plane for near objects and a far focal plane for distant objects, thereby permitting both near and far vision. The proximal side of the IOL can also be a plane or a concave surface in other embodiments of the present invention.

BRIEF DESCRIPTION OF THE DRAWING

Other objects and advantages of this invention will become more apparent from the following specification taken in conjunction with the drawing wherein:

FIG. 10 is a perspective view of the seventh embodiment using concentric spherical and aspherical sectors;

FIG. 11 is a median cross-sectional view thereof; and

FIG. 12 is an optical diagram illustrative of the various multifocal effects obtained with the seventh embodiment of the invention.

DESCRIPTION OF THE PREFERRED EMBODIMENTS OF THE INVENTION

Figures 1, 2, 3, 4:
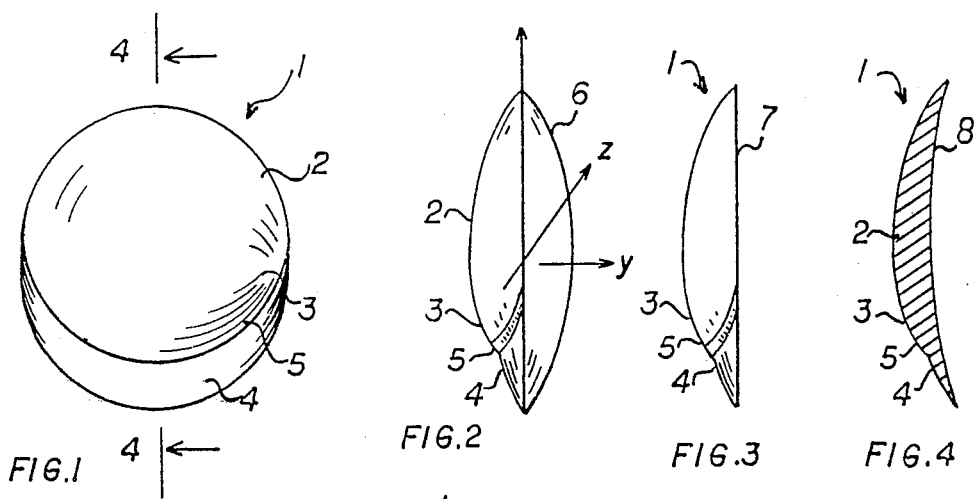
FIG. 1 is a front perspective view from the distal side of an intraocular lens common to the first, second and third preferred embodiments of the invention.
FIG. 2 is a side view of a first preferred embodiment of the present invention.
FIG. 3 is a side view of a second preferred embodiment of the present invention.
FIG. 4 is a cross-sectional view of a third preferred embodiment of the present invention taken along line 4—4 of FIG. 1.

Referring now to FIG. 1, there is represented a front perspective view from the distal side (or external side) of the intraocular lens of the present invention. The IOL of the present invention is particularly designed for the surgical correction of aphakia following extracapsular cataract extraction. This lenticulus is to be implanted in the posterior chamber of the patient's eye and is designed to be placed in the ciliary sulcus.

As illustrated in FIG. 1, the IOL of the present invention has the general shape of a biconvex disk. The distal side 1, represented in FIG. 1, has a generally spherical form with the exception of a sector 3 extending approximately from the mid-section of the distal side 1 to the lower quarter 4. The aspherical sector 3 is configured such that the radius of curvature decreases monotonously from the value $R_0$ of the radius of the upper spherical sector 2, to a lower value $R_1$. The lower spherical sector 4 has the same radius as the upper spherical sector 3, namely $R_0$. Because $R_0$ and $R_1$ are different, the aspherical sector 3 and the lower spherical sector 4 form an obtuse angle. $R_1$ varies typically between 7 mm and 9 mm, whereas $R_0$ varies between 8 mm and 10 mm radius of curvature in the preferred embodiments of the present invention. The discontinuity 5 between the aspherical sector 3 and the lower spherical quarter 4 is blocked out by dark or etched plastic in order to eliminate glare. However, the transition may be so slight as to preclude the need for any blocking or etching. The IOL is preferably made of polymethylmethacrylate (PMMA) or any other suitable material for IOL's such as silicon or hydrogel. The asphericity of the sector 3 not only occurs along the axis X of the intraocular lens, hereinafter referred as the vertical axis, but also along the axis Z of the lens, hereinafter referred as the horizontal axis. More particularly, the planes XY, XZ and YZ are respectively called hereinafter the vertical plane, the distal plane and the horizontal plane of the lens. The discontinuity 5 therefore extends from the lower quarter 4 to the mid-section of the lens on the edges and has an annular shape, as shown in FIG. 1.

Now turning to FIG. 2, there is illustrated the first embodiment of the present invention in a side view. The proximal side 6 is a convex surface in this embodiment. As illustrated in FIG. 1, the distal side 1 shows the three sectors hereabove described, namely the upper spherical sector 2, the central aspherical sector 3 and the lower spherical quarter 4.

In FIGS. 3 and 4, there are illustrated two other embodiments of the present invention. In FIG. 3, the proximal side 7 is a plane, whereas in FIG. 4, the proximal side 8 is a concave surface. In each of the aforementioned embodiments, the distal side has the same configuration.

Figure 5:
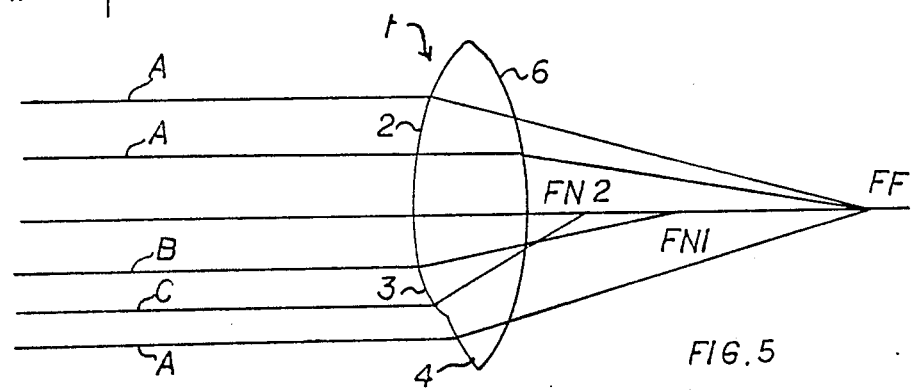
FIG. 5 is an optical diagram illustrative of the variable multifocal effect achieved by the first preferred embodiment of the present invention.

FIG. 5 is an explanatory optical diagram illustrating the multifocal property of the first preferred embodiment of the present invention as described hereabove. It should be noted, however, that the optical diagram of FIG. 5 holds true for the other embodiments of the present invention. A ray of light A impinging upon the lens on its spherical sector 2 is focused in the far focal plane, as indicated by FF. The aspherical sector is tangentially adjacent to the spherical sector 2 about the center of the mid-section of the IOL. As mentioned hereabove, the radius of curvature of the aspherical sector 3 varies from $R_0$, value of the radius of the spherical sector 2, to $R_1$. A ray of light C impinging upon the bottom of the aspherical sector is thus focused in a plane FN2 located between the lens and the far focal plane by virtue of elementary optical laws. The optic of the IOL of the present invention provides therefore both near vision through the aspherical sector 3 and distance vision through the spherical sectors 2 and 4. Light B from intermediate objects is also adequately focused in FN1 by the aspherical sector 3 because of its varying radius of curvature. The degree of sphericity can be chosen to permit a full dioptric range, thereby providing optimal post-operative vision. The principle underlying the functioning of the multifocal IOL herein disclosed, reposes on the general concept that the brain selects one or the other of the images focused on the retina by the IOL. This selection is based on differences in contrast between the images perceived by the brain. Through each of the sectors of the IOL, the focused image and the unfocused images are projected onto the retina, and the brain immediately selects the focused image. A loss of contrast is noticeable but not significant.

Figures 6, 7, 8, 9:
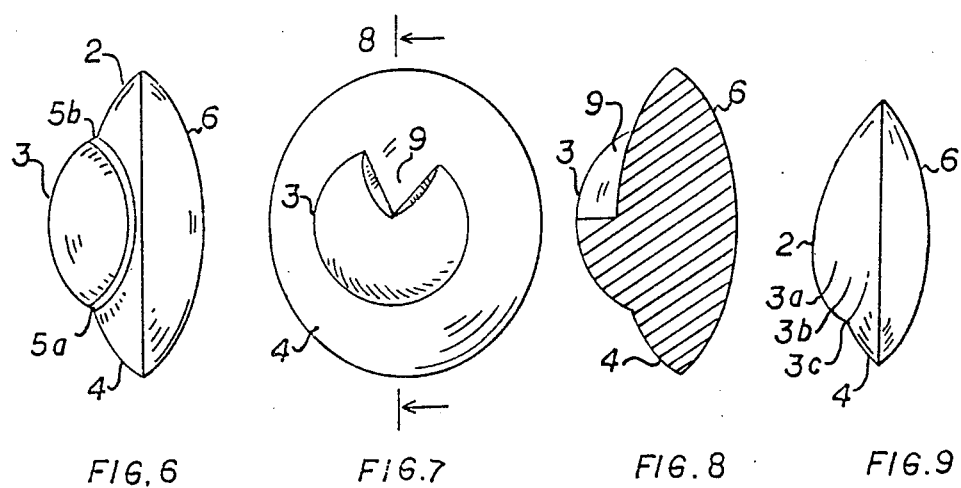
FIG. 6 is a side view of the fourth embodiment wherein the aspherical sector extends over the entire central part of the lens.
FIG. 7 is a perspective view of the fifth embodiment which includes an upper spherical angular sector.
FIG. 8 is a cross-sectional view thereof taken along line 8—8 of FIG. 7.
FIG. 9 is a side view of the sixth embodiment wherein the asphericity of the aspherical sector is achieved in discrete steps.

Now turning to FIG. 6, there is represented a side view of a fourth embodiment of the present invention wherein the aspherical sector 3 extends approximately from the lower quarter 4 to the upper quarter 2. This aspherical sector 3 therefore defines two discontinuities 5a and 5b which can be both blocked out to eliminate glare as stated hereinbefore.

In the fifth embodiment illustrated FIGS. 7 and 8, the aspherical sector 3 extends over the entirety of the central part of the intraocular lens as in FIG. 6 with the exception of an angular sector 9 in the upper part of the lens. More generally, the aspherical sector 9 can take various shapes. The number of degrees of the aspherical sector in the plane of the lenticulus can vary from 180 degrees to 360 degrees as in FIG. 6 and can take any intermediary value, as illustrated in FIG. 7. A value inferior to 180 degrees is not excluded but may impair the near vision properties of the intraocular lens.

Referring to FIG. 9, there is illustrated a sixth embodiment of the present invention similar to the first embodiment, but wherein the asphericity of the sector 3 is achieved in discrete steps. The aspherical sector extends from the lower quarter 4 to the mid-section 2 as in FIG. 2. However, the aspherical sector is constituted of three spherical domains 3a, 3b and 3c of decreasing value from $R_0$ to $R_1$. It should be understood that a greater number of discrete steps can be envisaged. In the example illustrated in FIG. 9, the spherical sectors 3a, 3b and 3c have respectively the following refractive powers: 1 diopter, 2 diopters and 3 diopters. Such an arrangement allows to obtain a continuum of refractive powers. Because the asphericity of the sector 3 extends both horizontally and vertically, the spherical sectors 3a, 3b and 3c take the form of concentric cresents around the center of the intraocular lens in the distal plane thereof.

FIGS. 10 through 11 illustrates a seventh embodiment of the invention using concentric spheric and aspheric zones. More specifically the intermediary sector 13 is aspherical, while the central sector 12 and peripheral sector 14 are spherical. As in the previously described embodiments, the radius of curvature of the aspherical sector 13 decreases progressively as we get close to the peripheral sector 14. This embodiment of the invention is symmetrical about all meridians. As the diagram of FIG. 12 indicates, the most distant focal point 15 corresponds to the spherical median and peripheral sectors 12 and 14, while the various proximal focal points 16, 17 correspond to the continuously variable aspherical sector 13.

It should be observed that minor variations of the aforedescribed IOL are envisageable, such as displacing upwards or downwards the three convex sectors hereabove described. In particular, the aspheric sector can be begin anywhere on the surface of the intraocular lens and be of any radius. In the embodiments hereinbefore described, the aspherical sector has the same radius as the lens itself and therefore extends from one edge of the lens to the other edge. A configuration wherein the aspherical sector occupies only the central part of the lens, is possible and would serve the same purpose as the embodiment more fully described hereabove. It should also be noted that the proximal side can be otherwise configured.

While the preferred embodiments of the invention have been described, modifications can be made and other embodiments may be devised within the spirit of the invention and the scope of the appended claims.

What is claimed is:

1. An intraocular implant to replace the crystalline lens of a patient's eye, in particular after a cataract extraction, comprising:

a generally discoidal biconvex lens shaped to exhibit light converging properties over its entirety;

said lens having a distal side and a proximal side to be placed against the vitreous humor of said patient's eye;

the face of one of said sides comprising:

a substantially aspherical, convex surface whereof the radius of curvature deceases from a value at points of said surface nearest to the center of the lens, to a lower value at points of said surface farther away from the center of the lens;

said decreases occurring along both the vertical axis and the horizontal axis of the plane of said lens.

2. The intraocular implant of claim 1, wherein said surface occupies the center of said distal side.

3. The intraocular implant of claim 1, wherein said surface extends over one half of the central part of said lens in the distal plane of said lens.

4. The intraocular implant of claim 1, wherein said surface is constituted of a series of successive spherical sectors, whereof the radii of curvature decrease discretely from the value of the radius of a first spherical sector nearest to the center of the lens to a lower value of the radius of the spherical sector further away from the center of the lens.

5. The intraocular implant of claim 1, wherein the radius of curvature in said surface is between 8 mm and 10 mm, and said lower value is between 7 and 9 mm.

6. The intraocular implant of claim 1, wherein, said surface includes a plurality of concentric aspherical and spherical sectors.

* * * * *